United States Patent [19]
Spaulding

[11] Patent Number: 5,871,553
[45] Date of Patent: Feb. 16, 1999

[54] FRAGRANCE-CARRIER COMPOSITIONS FOR USE IN TART CANDLES

[75] Inventor: Laura A. Spaulding, Wayne, N.J.

[73] Assignee: The Noville Corporation, South Hackensack, N.J.

[21] Appl. No.: 901,508

[22] Filed: Jul. 28, 1997

[51] Int. Cl.$^6$ .............................. C10L 11/00; C11C 5/00
[52] U.S. Cl. ............................. 44/275; 44/519; 431/288; 585/10; 585/12
[58] Field of Search ................................................ 44/275

[56] References Cited

U.S. PATENT DOCUMENTS

| | | | |
|---|---|---|---|
| 2,831,330 | 4/1958 | Walker | 44/275 |
| 3,411,855 | 11/1968 | Olund | 44/275 |
| 3,741,711 | 6/1973 | Bryant | 431/125 |
| 4,110,261 | 8/1978 | Newland | 44/275 |
| 5,578,089 | 11/1996 | Elsamaloty | 44/275 |

OTHER PUBLICATIONS

Scriven et al., (E, Z)–2,6–Nonadien–1–AL amd (E)–2–Nonen–1–AL Present in Crushed Cucumbers are Natural Repellents for the American Cochroach (*Periplaneta Americana*), Ohio J. Sci., vol. 84, No. 3, pp. 82–85 Jun. 1984.

Amoco Brochure, "Panalane Hydrogenated Polybutene—The Versatile Cosmetic Base Oil," 1992.(no month)

*Primary Examiner*—Ellen M. McAvoy
*Attorney, Agent, or Firm*—Kenyon & Kenyon

[57] ABSTRACT

The present invention is directed to pourable fragrance-carrier compositions, and methods of preparation thereof, for use in tart candles, wherein the fragrance-carrier composition is comprised of a liquid base material of a hydrogenated polyolefin and a fragrance. The fragrance-carrier composition may be poured into the reservoir of a tart candle from which the fragrance is caused to be dispersed by the heat from a flame. More specifically, the liquid base material is comprised of a hydrogenated polyisoalkene such as hydrogenated polyisobutene.

18 Claims, No Drawings

FRAGRANCE-CARRIER COMPOSITIONS FOR USE IN TART CANDLES

FIELD OF INVENTION

The present invention relates to fragrance-carrier compositions that are useful for dispensing fragrances. The fragrance-carrier compositions are preferably clear.

BACKGROUND OF THE INVENTION

Compositions that are used as carriers for dispensing fragrances from a heated reservoir, such as in a tart candle, are typically comprised of materials that, while they have a high throwing power for dispensing the desired fragrance, may also have certain disadvantages. In particular, though these carrier compositions are specifically intended for use in dispensing fragrances that have a pleasant or a particularly desired odor, the compositions may include base materials which themselves have a strong unpleasant odor. In such cases, the fragrance is required, in part, simply to mask the undesired odors of the base material. As a result, such masking may reduce the benefit provided by the fragrance and/or require higher levels of the fragrance than might otherwise be desired.

It would be desirable to have fragrance-carrier compositions comprised of safe odorless base materials that have a high throwing power for diffusing fragrances.

The present invention is directed toward fragrance carrier compositions that provide these advantages while not being handicapped with the above-noted disadvantages.

ADVANTAGES AND SUMMARY OF THE INVENTION

The present invention is directed to fragrance carrier compositions, and methods of preparation thereof, which are comprised of clear, colorless, and odorless base materials for safely dispensing fragrances with a high throwing power.

Yet more specifically, the present invention is directed to liquid base materials that can be readily provided in conveniently disposable containers.

More specifically, the present invention is directed to liquid base materials comprised of hydrogenated polyolefins that are particularly effective for use as fragrance-carrier compositions. Still more specifically, the fragrance-carrier compositions are comprised of hydrogenated polyisobutenes as the predominant component, wherein the polyisobutene may be comprised of two grades of polyisobutene, with the major fraction being of high viscosity and the minor fraction being of low viscosity.

Further objectives and advantages of the subject invention will be apparent to those skilled in the art from the detailed description of the disclosed invention.

DETAILED DESCRIPTION OF THE PREFERRED EMBODIMENTS

The subject invention will now be described in detail for specific preferred embodiments of the invention, it being understood that these embodiments are intended only as illustrative examples and the invention is not to be limited thereto.

The fragrance-carrier compositions of the present invention, which are useful because of their high throwing power for dispensing fragrances and because of their relative lack of a tendency to auto-ignite, are comprised of a clear and odorless liquid base material. A scented composition, in which a fragrance is dissolved in the liquid base material, may be placed in a reservoir which resides above a flame produced by a tea light or votive type candle, which is known in the art as a "tart candle". The term "tart candle" is used herein to refer to any type of application in which a reservoir containing a fragrance-carrier composition is placed above a flame that causes the fragrance to be diffused into the surrounding environment. The flame heats the liquid thus causing the fragrance to be slowly and continuously vaporized. The liquid base materials of the present invention are particularly suitable as fragrance carriers due to their inherently safe characteristics, especially as compared with the clear fragrance-carrier compositions of the prior art which tend to auto-ignite or which contain base materials that produce unpleasant odors.

Though the present invention is described herein in terms of the fragrance-carrier composition typically being used in a tart candle in which heat is provided by a flame, it is to be understood that still other types of heat sources may be used in combination with the fragrance-carrier compositions while still remaining within the scope and spirit of the present invention.

In a representative embodiment of the present invention, the base material is comprised of a hydrocarbon composition that is a clear, colorless and odorless liquid at ambient temperature. In particular, the base material is comprised predominantly of a hydrogenated polyolefin. The degree of hydrogenation is preferably such as to produce a substantially fully saturated polyolefin. Though experiments have not been conducted to quantitatively determine the degree of hydrogenation that provides the most desired results for the present invention, it is believed that the polyolefin needs to have at least 90% of the free olefinic groups of the polyolefin saturated by hydrogenation, even though it is also believed that only about 10% hydrogenation of the free olefinic group of the polyolefin may be acceptable under certain circumstances.

In a preferred embodiment of the subject invention, the base material is comprised of hydrogenated polyisobutene, which is commercially available under the name PANALANE™. The repeating unit of hydrogenated polyisobutene is shown by the following chemical structure:

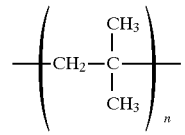

Hydrogenated polyisobutene is commercially available as PANALANE™ from Lipo Chemical of Paterson, N.J. or as INDOPOL™ from the Amoco Chemical Company, Chicago, Ill. The The hydrogenated polyisobutene PANALANE™ from Lipo Chemical is available in two grades, as a higher viscosity component, Grade H-300E, where the average number of repeating units is about 23, or as a lower viscosity component, Grade L-14E, where the average number of repeating units is about 6 to 8.

In a preferred embodiment, the base material is comprised of the higher viscosity component as the major proportion and the lower viscosity component as the minor proportion. The ratio of the higher viscosity fraction to the lower viscosity fraction may be determined to be that which provides the desired balance between a high enough viscosity for effectively retaining the fragrance without substantial loss of the fragrance during storage and a low enough viscosity for pouring, as well as for producing a high throwing power of the fragrance when the reservoir is heated. Thus, while there may be preferred ranges for the ratio of the higher viscosity component to the lower viscosity component, dependent on the viscosity desired for the fragrance-carrier composition and on the specific fragrance, the fragrance-carrier composition may be comprised substantially entirely either of the higher viscosity component or of the lower viscosity component. In particular, for a liquid that may be poured into the reservoir of a tart candle, the range for the higher viscosity component may be from about 0 wt. % to about 99.99 wt. % and the lower viscosity component may be from about 99.99 wt. % to about 0 wt. %, respectively. The fragrance may be present in a range from about 0.01 wt. % up to about 10 wt. %. In a preferred embodiment of the present invention, the fragrance-carrier composition is comprised of about 90 wt. % of a higher viscosity hydrogenated polyisobutene, such as PANALANE™ H300E, about 3 wt. % of a lower viscosity hydrogenated polyisobutene, such as PANALANE™ L14E and about 3 wt. % fragrance.

The preferred liquid base material of the present invention, hydrogenated polyisobutene, has the advantage of being readily available in commercial quantities as an ingredient that is listed in the Cosmetic Toiletry and Fragrance Associate Ingredient Dictionary, having a CAS number of 68937-10-0. The odorless, low volatility base materials of the present invention are, thus, recognized as toxicologically safe for use in the cosmetic arts. Furthermore, the base materials of the present invention have no tendency to auto-ignite. Such auto-ignition, which is caused by excessive fumes emanating from the surface, may occur with certain prior art tart candle compositions, such as those which use kerosene, lamp oil or a mineral oil/styrene/rubber copolymer mix.

Though the liquid base materials of the present invention are specifically disclosed in the preferred embodiments as being comprised of high and low viscosity fractions of hydrogenated polyisobutenes, which are recognized as toxicologically safe and readily available as commercial materials in the cosmetic arts, it is to be understood that the hydrogenated polyisobutenes are representative of a much broader class of compounds which fall fully within the scope and spirit of the present invention. In particular, the present invention is directed to fragrance-carrier compositions prepared from liquid base materials comprised of hydrogenated polyolefins generally. Preferably, the hydrogenated polyolefins are hydrogenated polyalkenes which are substantially free of phenyl groups in the chemical structure, especially, polyalkenes in which, because of their odiferous properties, there are no phenyl groups in the repeating unit. Still more preferably, the hydrogenated polyalkenes are hydrogenated polyisoalkenes. The term "polyisoalkenes" refers to polyalkenes which include a skeletal isocarbon in the repeating unit of the polyalkene. A skeletal "isocarbon" is a skeletal carbon atom that is chemically bound to three carbon atoms in the repeating unit. Preferably, substantially all the olefinic bonds of the polyolefin are hydrogenated so as to produce a fully saturated polyolefin. Fully saturated is herein understood to mean at least 90% of the free olefinic groups of the polyolefin are saturated by hydrogenation.

The liquid base materials are further comprised of a fragrance that may be selected because of its pleasing odor or because of its effectiveness as an insect repellant. Particularly pleasing fragrances include, for example, F37028 Sweet Peach, F37950 Mountain Berry, F37953 Country Garden, which are available from Noville Corporation of South Hackensack, N.J. Such fragrances are typically added in the range from about 1 wt. % to about 5 wt. %, with the level being selected so as to achieve the desired throwing power. Examples of insect repellants include citronella or an extract that is present in crushed cucumbers, that is, (E,Z)-2,5-nonadien-1-al and (E)-2-nonen-1-al, which is an effective natural repellant for cockroaches.

The fragrance-carrier compositions may be prepared by adding the components of the liquid base material to a mixing vessel which can be heated and, if desired, agitated. For example, if the liquid base material is comprised of a higher and lower viscosity component of hydrogenated polyisobutene, the materials are added in the desired ratio and heated with agitation to a temperature that is suitable for adding the fragrance. Since the fragrance is typically available in combination with a carrier, the liquid base material needs to be heated to a temperature that permits the fragrance and its carrier to be readily solubilized. For a mixture of higher and lower viscosity components of hydrogenated polyisobutene, a temperature of about 45°–50° C. is typically sufficient. Preferably, the temperature is not too high such as to cause the fragrance to be lost by vaporization during preparation of the fragrance-carrier composition. When the base material reaches a suitable temperature, the heating is discontinued and the fragrance is then added and mixed until the composition becomes homogeneous. After the fragrance is fully solubilized, the pourable liquid composition is ready for use in the reservoir of a tart candle. The fragrance-carrier composition may then be transferred, either before or after cooling to ambient temperature, to an appropriate container for shipment and storage until it is ready to be used.

The pourable liquids prepared in this manner have acceptable fragrance compatibility, odor aesthetics and exceptional fragrance throw. The term "fragrance throw" is also referred to in the art as "fragrance dispersion".

The subject invention as disclosed herein may be used in conjunction with the co-pending application entitled "Clear Gel Formulations For Use In Transparent Candles", Attorney Docket No. 10209/1, Ser. No. 08/901,449, which is filed on the same date as the present application, the co-pending application being incorporated herein by reference in its entirety.

This invention will now be described in detail with respect to showing how certain specific representative embodiments thereof will be made, the materials, apparatus and process steps being understood as examples that are intended to be illustrative only. In particular, the invention is not intended to be limited to the methods, materials, conditions, process parameters, apparatus and the like specifically recited herein.

AN EXAMPLE OF THE INVENTION

A representative fragrance-carrier composition was made having the following formulation:

90 wt. % higher viscosity hydrogenated polyisobutene (PANALANE™ H300E)

7 wt. % lower viscosity hydrogenated polyisobutene (PANALANE™ L14E) L14E and 3 wt % Fragrance.

A formulation using an extract that is present in crushed cucumbers, (E,Z)-2,5-nonadien-1-al and (E)-2-nonen-1-al, was prepared.

What is claimed is:

1. A fragrance-carrier composition for use in a reservoir of a tart candle comprising a liquid base material comprised of a hydrogenated polyolefin and a fragrance.

2. The fragrance-carrier composition of claim 1 wherein the hydrogenated polyolefin is a hydrogenated polyalkene.

3. The fragrance-carrier composition of claim 1 wherein the hydrogenated polyalkene is a hydrogenated polyisoalkene.

4. The fragrance-carrier composition of claim 1 wherein the hydrogenated polyisoalkene is a hydrogenated polyisobutene that has a repeating unit having the following chemical structure:

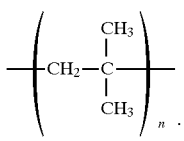

5. The fragrance-carrier composition of claim 4 wherein the hydrogenated polyisobutene is comprised of a higher viscosity component and a lower viscosity component.

6. The fragrance-carrier composition of claim 5 wherein the average number of repeating units of the higher viscosity component is about 23.

7. The fragrance-carrier composition of claim 5 wherein the average number of repeating units of the lower viscosity component is about 6 to 8.

8. The fragrance-carrier composition of claim 1 wherein the liquid base material is comprised predominantly of a hydrogenated polyolefin.

9. A tart candle for dispensing fragrances comprising a reservoir containing the fragrance-carrier composition of claim 1.

10. A method of preparing a fragrance-carrier composition for use in a reservoir of a tart candle comprising:

adding a liquid base material to a mixing vessel;

and solubilizing a fragrance in the liquid base material;

wherein the liquid base material is comprised of a hydrogenated polyolefin.

11. The method according to claim 10 wherein the hydrogenated polyolefin is a hydrogenated polyalkene.

12. The method according to claim 10 wherein the hydrogenated polyalkene is a hydrogenated polyisoalkene.

13. The method according to claim 10 wherein the hydrogenated polyisoalkene is a hydrogenated polyisobutene that has a repeating unit having the following chemical structure:

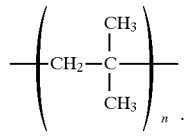

14. The method according to claim 13 wherein the hydrogenated polyisobutene is comprised of a higher viscosity component and a lower viscosity component.

15. The method according to claim 14 wherein the average number of repeating units of the higher viscosity component is about 23.

16. The method according to claim 14 wherein the average number of repeating units of the lower viscosity component is about 6 to 8.

17. The method according to claim 10 wherein the liquid base material is comprised predominantly of a hydrogenated polyolefin.

18. A fragrance-carrier composition for use in a reservoir of a tart candle comprising a liquid base material comprised of a hydrogenated polyisobutene that has a repeating unit having the following chemical structure:

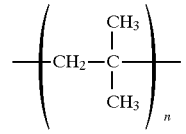

and a fragrance, wherein a higher viscosity component of the hydrogenated polyisobutene having an average number of repeating units of about 23 comprises about 90 wt. % of the total fragrance-carrier composition, a lower viscosity component of the hydrogenated polyisobutene having an average number of repeating units of about 6 to 8 comprises about 7 wt. % of the total fragrance-carrier composition and the fragrance comprises about 3 wt. % of the total fragrance-carrier composition.

* * * * *